United States Patent
Kulkarni et al.

(10) Patent No.: US 7,864,968 B2
(45) Date of Patent: Jan. 4, 2011

(54) AUDITORY FRONT END CUSTOMIZATION

(75) Inventors: Abhijit Kulkarni, Newbury Park, CA (US); Lakshimi Narayan Mishra, Valencia, CA (US); Michael A. Faltys, Northridge, CA (US)

(73) Assignee: Advanced Bionics, LLC, Valencia, CA (US)

( * ) Notice: Subject to any disclaimer, the term of this patent is extended or adjusted under 35 U.S.C. 154(b) by 1121 days.

(21) Appl. No.: 11/535,004

(22) Filed: Sep. 25, 2006

(65) Prior Publication Data

US 2008/0085023 A1    Apr. 10, 2008

(51) Int. Cl.
H04R 29/00    (2006.01)
H04B 15/00    (2006.01)
H03B 29/00    (2006.01)
A61N 1/00    (2006.01)

(52) U.S. Cl. .................. 381/60; 381/94.9; 381/71.9; 607/57

(58) Field of Classification Search .................. 607/57; 600/25, 559; 381/23.1, 60, 71.8, 71.9, 92, 381/94.9, 314, 320, 326; 327/551; 708/309, 708/314, 321

See application file for complete search history.

(56) References Cited

U.S. PATENT DOCUMENTS

| | | | |
|---|---|---|---|
| 3,751,605 A | 8/1973 | Michelson |
| 4,051,330 A | 9/1977 | Cole |
| 4,400,590 A | 8/1983 | Michelson |
| 4,495,384 A | 1/1985 | Scott et al. |
| 4,532,930 A | 8/1985 | Crosby et al. |
| 4,793,353 A | 12/1988 | Borkan |
| 4,819,647 A | 4/1989 | Byers et al. |
| 5,033,090 A | 7/1991 | Weinrich |
| 5,201,006 A | 4/1993 | Weinrich |
| 5,204,917 A | 4/1993 | Arndt et al. |
| 5,357,576 A | 10/1994 | Arndt |
| 5,597,380 A | 1/1997 | McDermott et al. |
| 5,601,617 A | 2/1997 | Loeb et al. |
| 5,603,726 A | 2/1997 | Schulman et al. |
| 5,626,629 A | 5/1997 | Faltys et al. |

(Continued)

FOREIGN PATENT DOCUMENTS

WO    96/39005    5/1996

(Continued)

OTHER PUBLICATIONS

U.S. Appl. No. 10/178,010, filed Jun. 20, 2002.

(Continued)

Primary Examiner—Curtis Kuntz
Assistant Examiner—Jesse A Elbin
(74) Attorney, Agent, or Firm—Wong, Cabello, Lutsch, Rutherford & Brucculeri LLP

(57) ABSTRACT

A method and system for implementing an acoustical front end customization are disclosed. The customization is implemented to optimize the sound level for each individual cochlear implant user. A known audio signal is generated using a sound source and captured by a microphone system. The captured sound signal is sampled at one or more locations along the signal processing pathway, and a spectrum is determined for the sampled signal and the known signal. A ratio of the two spectrums is related to the undesired transformation of the sampled signal, and a digital filter is designed based on the ratio to filter out the undesired transformation.

20 Claims, 8 Drawing Sheets

U.S. PATENT DOCUMENTS

| | | | |
|---|---|---|---|
| 5,749,912 | A | 5/1998 | Zhang et al. |
| 5,824,022 | A | 10/1998 | Zilberman et al. |
| 5,876,425 | A | 3/1999 | Gord et al. |
| 5,938,691 | A | 8/1999 | Schulman et al. |
| 5,991,663 | A | 11/1999 | Irlicht et al. |
| 6,002,966 | A | 12/1999 | Loeb et al. |
| 6,067,474 | A | 5/2000 | Schulman et al. |
| 6,078,838 | A | 6/2000 | Rubinstein |
| 6,129,753 | A | 10/2000 | Kuzma |
| 6,154,678 | A | 11/2000 | Lauro |
| 6,157,861 | A | 12/2000 | Faltys et al. |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,216,045 | B1 | 4/2001 | Black et al. |
| 6,219,580 | B1 | 4/2001 | Faltys et al. |
| 6,272,382 | B1 | 8/2001 | Faltys et al. |
| 6,289,247 | B1 | 9/2001 | Faltys et al. |
| 6,295,467 | B1 | 9/2001 | Kollmeier et al. |
| 6,308,101 | B1 | 10/2001 | Faltys et al. |
| 6,415,185 | B1 | 7/2002 | Maltan |
| 6,522,764 | B1 | 2/2003 | Bøgeskov-Jensen |
| 6,600,955 | B1 | 7/2003 | Zierhofer |
| 6,658,125 | B1 | 12/2003 | Batting |
| 6,700,983 | B1 | 3/2004 | Bøgeskov-Jensen |
| 6,728,578 | B1 | 4/2004 | Voelkel |
| 6,735,474 | B1 | 5/2004 | Loeb et al. |
| 6,745,155 | B1 | 6/2004 | Andringa et al. |
| 6,775,389 | B2 | 8/2004 | Harrison et al. |
| 6,778,858 | B1 | 8/2004 | Peeters |
| 6,826,430 | B2 | 11/2004 | Faltys et al. |
| 6,842,647 | B1 | 1/2005 | Griffith et al. |
| 6,980,864 | B2 | 12/2005 | Faltys et al. |
| 7,039,466 | B1 | 5/2006 | Harrison et al. |
| 7,043,303 | B1 | 5/2006 | Overstreet |
| 7,043,304 | B1 | 5/2006 | Griffith et al. |
| 7,054,691 | B1 | 5/2006 | Kuzma et al. |
| 7,076,308 | B1 | 7/2006 | Overstreet et al. |
| 7,107,101 | B1 | 9/2006 | Faltys |
| 2001/0031909 | A1 | 10/2001 | Faltys et al. |
| 2003/0036782 | A1 | 2/2003 | Hartley et al. |
| 2003/0044034 | A1 | 3/2003 | Zeng et al. |
| 2003/0167077 | A1 | 9/2003 | Blamey et al. |
| 2003/0171786 | A1 | 9/2003 | Blamey et al. |
| 2003/0179891 | A1 | 9/2003 | Rabinowitz et al. |
| 2003/0229383 | A1 | 12/2003 | Whitehurst et al. |
| 2004/0044383 | A1 | 3/2004 | Woods et al. |
| 2004/0073275 | A1 | 4/2004 | Maltan et al. |
| 2004/0082980 | A1 | 4/2004 | Mouine et al. |
| 2004/0082985 | A1 | 4/2004 | Faltys et al. |
| 2004/0114776 | A1 | 6/2004 | Crawford et al. |
| 2004/0136556 | A1 | 7/2004 | Litvak et al. |
| 2004/0162691 | A1 * | 8/2004 | Pupalaikis et al. .......... 702/106 |
| 2004/0172101 | A1 | 9/2004 | Van Hoesel |
| 2004/0230254 | A1 | 11/2004 | Harrison et al. |
| 2005/0063555 | A1 | 3/2005 | Berardi et al. |
| 2005/0102006 | A1 | 5/2005 | Whitehurst et al. |
| 2005/0119716 | A1 | 6/2005 | McClure et al. |
| 2005/0131494 | A1 | 6/2005 | Park et al. |
| 2005/0137650 | A1 | 6/2005 | Litvak et al. |
| 2005/0137651 | A1 | 6/2005 | Litvak et al. |
| 2005/0143781 | A1 | 6/2005 | Carbunaru et al. |
| 2005/0213780 | A1 | 9/2005 | Berardi et al. |
| 2005/0245991 | A1 | 11/2005 | Faltys et al. |
| 2005/0251225 | A1 | 11/2005 | Faltys et al. |
| 2005/0267549 | A1 | 12/2005 | Della Santina et al. |
| 2005/0271215 | A1 | 12/2005 | Kulkami |
| 2006/0100672 | A1 | 5/2006 | Litvak et al. |
| 2006/0167963 | A1 * | 7/2006 | Bruno et al. ................ 708/300 |
| 2006/0184212 | A1 | 8/2006 | Faltys et al. |
| 2006/0276719 | A1 | 12/2006 | Litvak et al. |

FOREIGN PATENT DOCUMENTS

| | | |
|---|---|---|
| WO | 96/34508 | 10/1996 |
| WO | 97/48447 | 6/1997 |
| WO | 01/74278 | 10/2001 |
| WO | 03/015863 | 2/2003 |
| WO | 03/018113 | 3/2003 |
| WO | 03/030772 | 4/2003 |
| WO | 2004/043537 | 5/2004 |
| WO | 2005/097255 | 10/2005 |
| WO | PCT/US2005/040688 | 11/2005 |
| WO | 2006/053101 | 5/2006 |
| WO | PCT/US2006/034652 | 9/2006 |

OTHER PUBLICATIONS

U.S. Appl. No. 10/176,722, filed Jun. 20, 2002.
U.S. Appl. No. 10/176,743, filed Jun. 20, 2002.
U.S. Appl. No. 10/178,011, filed Jun. 20, 2002.
U.S. Appl. No. 10/285,803, filed Nov. 1, 2002.
U.S. Appl. No. 10/982,371, filed Nov. 5, 2004.
U.S. Appl. No. 10/981,944, filed Nov. 5, 2004.
U.S. Appl. No. 10/992,625, filed Nov. 17, 2004.
U.S. Appl. No. 10/992,390, filed Nov. 17, 2004.
U.S. Appl. No. 11/003,155, filed Dec. 3, 2004.
U.S. Appl. No. 11/008,869, filed Dec. 9, 2004.
U.S. Appl. No. 11/016,604, filed Dec. 16, 2004.
U.S. Appl. No. 11/089,171, filed Mar. 24, 2005.
U.S. Appl. No. 11/122,648, filed May 5, 2005.
U.S. Appl. No. 11/130,644, filed May 16, 2005.
U.S. Appl. No. 11/139,296, filed May 26, 2005.
U.S. Appl. No. 11/178,054, filed Jul. 8, 2005.
U.S. Appl. No. 11/221,095, filed Sep. 6, 2005.
U.S. Appl. No. 11/226,777, filed Sep. 13, 2005.
U.S. Appl. No. 11/261,432, filed Oct. 28, 2005.
U.S. Appl. No. 11/262,055, filed Oct. 28, 2005.
U.S. Appl. No. 11/291,464, filed Nov. 30, 2005.
U.S. Appl. No. 11/386,198, filed Mar. 21, 2006.
U.S. Appl. No. 11/387,206, filed Mar. 23, 2006.
U.S. Appl. No. 11/388,836, filed Mar. 24, 2006.
U.S. Appl. No. 11/418,847, filed May 5, 2006.
U.S. Appl. No. 11/536,565, filed Sep. 28, 2006.
U.S. Appl. No. 11/534,933, filed Sep. 25, 2006.
Carney, L.H., "A model for the responses of low-frequency auditory-nerve fibers in cat," Journal of the Acoustic Society of America, 93(1):401-417, (1993).
Deutsch, et al.(Eds.) *Understanding the Nervous System, An Engineering Perspective*, New York, N.Y: IEEE Press, pp. 181-225, (1993).
Geurts, L. and J. Wouters, "Enhancing the speech envelope of continuous interleaved sampling processors for cochlear implants," Journal of the Acoustic Society of America, 105(4):2476-2484, (1999).
Moore, Brian C.J., *An Introduction to the Psychology of Hearing*, San Diego, CA: Academic Press, pp. 9-12, (1997).
Rubinstein, J.T., et al., "The Neurophysiological Effects of Simulated Auditory Prosthesis Simulation," Second Quarterly Progress Report: NO1-DC-6-2111, (May 27, 1997).
Srulovicz et al., "A Central Spectrum Model: A Synthesis of Auditory-Nerve Timing and Place Cues in Monaural Communication of Frequency Spectrum", Journal of the Acoustic Society of America, 73(4):1266-1276, (1983).
van Wieringen, et al., "Comparison of Procedures to Determine Electrical Stimulation Thresholds in Cochlear Implant Users", Ear and Hearing, 22(6):528-538, (2001).
Zeng, et al., "Loudness of Simple and Complex Stimuli in Electric Hearing", Annals of Otology, Rhinology & Laryngology, 104 (No. 9, Part 2, Suppl. 166):235-238, (1995).

* cited by examiner

AUDITORY FRONT END CUSTOMIZATION

TECHNICAL FIELD

The present disclosure relates to implantable neurostimulator devices and systems, for example, cochlear stimulation systems, and to sound processing strategies employed in conjunction with such systems.

BACKGROUND

Prior to the past several decades, scientists generally believed that it was impossible to restore hearing to the profoundly deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech. The electrical stimulation is implemented through a prosthetic device, known as a cochlear implant (CI), which is implanted in the inner ear to restore partial hearing.

Cochlear implants generally employ an electrode array that is inserted into the cochlear duct. One or more electrodes of the array selectively stimulate the auditory nerve along different places in the cochlea based on the frequency of a received acoustic signal picked up by a microphone and transformed to an electrical signal by a digital signal processor (DSP) unit located in the external ear piece of a cochlear implant front end.

After a patient has been provided with a CI, it is necessary to initially "fit" or "adjust" the device during a fitting session. As used herein, it should be noted that terms "fit", "adjust", "fitting", "adjusting", "program", or "programming" relate to making electronic or software programming changes to the CI device. A proper fitting is essential to ensuring the CI user experience natural sound quality. Currently, the fitting session suffers from inefficiency and subjectivity for a few reasons. Because a new CI user is used to experiencing either poor sound quality or no sound at all, he/she finds it difficult to qualitatively communicate a perceived sound quality and preference to a technician during the fitting session. This results in a fitted device not accurately tailored to the specific CI user. Worst yet, younger CI users (i.e. children) are incapable of communicating effectively the nature of experienced sound quality to the technician.

Characteristics of a cochlear implant front's end play an important role in the perceived sound quality (and hence speech recognition or music appreciation) experienced by the CI user. These characteristics are governed by the components of the front-end comprising a microphone, an A/D converter, and the acoustic effects resulting from a location of the microphone on the user's head. While the component characteristics meet pre-defined standards, and can hence be compensated for, the acoustic characteristics are unique to the CI user's anatomy and his/her placement of the microphone on their head. Specifically, the unique shaping of the user's ears and head geometry can result in substantial shaping of the acoustic waveform picked up by the microphone. Because this shaping is unique to the CI user and his/her microphone placement, it cannot be compensated for with a generalized solution. This issue can be even more critical in beamforming applications where signals from multiple microphones are combined to achieve a desired directivity. It is critical for the multiple microphones in these applications to have matched responses. Any differences in the microphones' responses due to their placement on the patient's head can make this challenging.

SUMMARY

The methods and systems described here implement techniques for optimizing sound levels as perceived through a cochlear implant. For example, the techniques are implemented to customize an acoustical front end for each individual cochlear implant user.

In one aspect, a known audio signal is generated using a sound source and the generated audio signal is captured by a microphone system. The captured sound signal is processed along one or more signal paths, and the processed signal is sampled at one or more locations along the signal processing pathway. Comparisons are made between the generated known audio signal and the sampled signal to determine the undesired transformation of the sampled signal. Based on the comparisons, a digital filter is designed to filter out the undesired transformation and customizing the acoustical front end for the individual cochlear implant user.

Implementations can include one or more of the following features. For example, the known audio signal can be generated through an external sound source. Also, the captured audio signal can be processed by converting the known audio signal into an analog electrical signal; converting the analog electrical signal into a digital signal; and adjusting a gain of the digital signal. In addition, processed audio signal can be sampled before adjusting the gain of the digital signal or after adjusting the gain of the digital signal or both. Further, the sampled audio signal can be compared against the known audio signal by generating a spectrum of the sampled audio signal; generating a spectrum of the known audio signal; and determining a ratio of the sampled audio signal spectrum over the known audio signal spectrum. Based on the determined ratio, the filter can be generated.

Implementations can also include one or more of the following features. For example, the processed signal can be sampled at two or more locations along the signal path. In addition, the captured audio signal can be processed along two or more signal paths in parallel. Further, the filter can be generated to optimally match a first response of a first microphone with a second response of a second microphone. The first and second responses of the first and second microphones comprises a beamformer to provide directivity of the captured signal.

The techniques described in this specification can be implemented to realize one or more of the following advantages. For example, the techniques can be implemented to eliminate the need to physically match the microphones at the manufacturing stage. The techniques can also be implemented to provide a tailored fitting for individual CI user. The techniques also can be implemented to eliminate unknown loading effects due to the positioning of the two microphones and physiology of the patient's head. The unknown loading effects created on the microphones results in unmatched responses even if the two microphones of a beam forming device are perfectly matched. Further, the techniques can be implemented to compensate for the physiological effect. In addition, a microphone test mode allows the user to run active or dynamic check/test of the microphone.

These general and specific aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION

Figure 1:
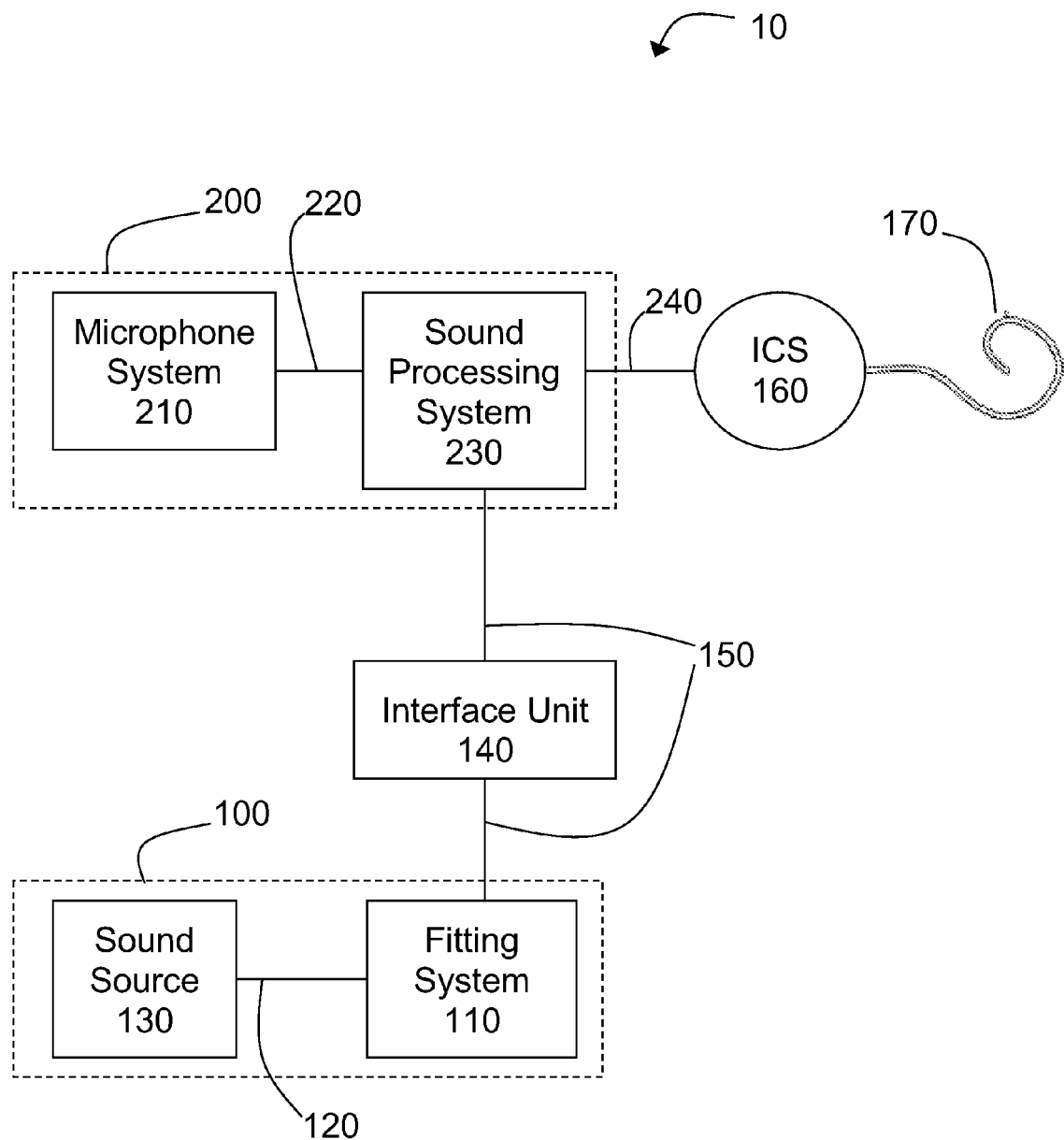
FIG. 1 is a functional block diagram of an auditory front end customization system.

FIG. 1 depicts an auditory front end customization system 10 comprising a fitting portion 100 in communication with a sound processing portion 200. The fitting portion 100 can include a fitting system 110 communicatively linked to an external sound source 130 using an appropriate communication link 120. The fitting system 110 may be substantially as shown and described in U.S. Pat. Nos. 5,626,629 and 6,289,247, both patents incorporated herein by reference. In general, the fitting system 110 is implemented on a computer system located at an office of an audiologist or a medical personnel and used to perform an initial fitting or customization of a cochlear implant for a particular user. The sound processing portion 200 is implemented on a behind the ear (BTE) headpiece, which is shown and described in U.S. Pat. No. 5,824,022, the patent incorporated herein by reference. The sound processing portion can include a microphone system 210 communicatively linked to a sound processing system 230 using a suitable communication link 220. The fitting system 110 is coupled to the sound processing system 230 through an interface unit (IU) 140, or an equivalent device. A suitable communication link 150 couples the interface unit 140 with the sound processing system 230 and the fitting system 110. The IU can be included within the computer as a built-in I/O port including but not limited to an IR port, serial port, a parallel port, and a USB port.

The fitting portion 100 can generate an acoustic signal, which can be picked up and processed by the sound processing portion 200. The processed acoustic signal can be passed to an implantable cochlear stimulator (ICS) 160 through an appropriate communication link 240. The ICS 160 is coupled to an electrode array 170 configured to be inserted within the cochlea of a patient. The implantable cochlear stimulator 170 can apply the processed acoustic signal as a plurality of stimulating inputs to a plurality of electrodes distributed along the electrode array 170. The electrode array 170 may be substantially as shown and described in U.S. Pat. Nos. 4,819,647 and 6,129,753, both patents incorporated herein by reference. The sound processing portion 200 may be substantially as shown and described in the co-pending U.S. patent application Ser. No. 11/003,155.

In some implementations, both the fitting portion 100 and the sound processing portion 200 are implemented in the external BTE headpiece. The fitting portion 100 can be controlled by a hand-held wired or wireless remote controller device (not shown) by the medical personnel or the cochlear implant user. The implantable cochlear stimulator 160 and the electrode array 170 can be an internal, or implanted portion. Thus, a communication link 240 coupling the sound processing system 230 and the internal portion can be a transcutaneous (through the skin) link that allows power and control signals to be sent from the sound processing system 230 to the implantable cochlear stimulator 160.

In some implementations, the sound processing portion 200 may be incorporated into an internally located implantable cochlear system (not shown).

The implantable cochlear stimulator can send information, such as data and status signals, to the sound processing system 230 over the communication link 240. In order to facilitate bidirectional communication between the sound processing system 230 and the implantable cochlear stimulator 160, the communication link 240 can include more than one channel. Additionally, interference can be reduced by transmitting information on a first channel using an amplitude-modulated carrier and transmitting information on a second channel using a frequency-modulated carrier.

The communication links 120 and 220 are wired links using standard data ports such as Universal Serial Bus interface, IEEE 1394 FireWire, or other suitable serial or parallel port connections.

In some implementations, the communication links 120 and 220 are wireless links such as the Bluetooth protocol. The Bluetooth protocol is a short-range, low-power 1 Mbit/sec wireless network technology operated in the 2.4 GHz band, which is appropriate for use in piconets. A piconet can have a master and up to seven slaves. The master transmits in even time slots, while slaves transmits in odd time slots. The devices in a piconet share a common communication data channel with total capacity of 1 Mbit/sec. Headers and handshaking information are used by Bluetooth devices to strike up a conversation and find each other to connect.

Other standard wireless links such as infrared, wireless fidelity (Wi-Fi), or any other suitable wireless connections can be implemented. Wi-Fi refers to any type of IEEE 802.11 protocol including 802.11a/b/g/n. Wi-Fi generally provides wireless connectivity for a device to the Internet or connectivity between devices. Wi-Fi operates in the unlicensed 2.4 GHz radio bands, with an 11 Mbit/sec (802.11b) or 54 Mbit/sec (802.11a) data rate or with products that contain both bands. Infrared refers to light waves of a lower frequency out of range of what a human eye can perceive. Used in most television remote control systems, information is carried between devices via beams of infrared light. The standard infrared system is called infrared data association (IrDA) and is used to connect some computers with peripheral devices in digital mode.

In implementations whereby the implantable cochlear stimulator 160 and the electrode array 170 are implanted within the CI user, and the microphone system 210 and the sound processing system 230 are carried externally (not implanted) by the CI user, the communication link 240 can be realized through use of an antenna coil in the implantable cochlear stimulator and an external antenna coil coupled to the sound processing system 230. The external antenna coil can be positioned to be in alignment with the implantable cochlear stimulator, allowing the coils to be inductively coupled to each other and thereby permitting power and information, e.g., the stimulation signal, to be transmitted from the sound processing system 230 to the implantable cochlear stimulator 160.

In some implementations, the sound processing system 230 and the implantable cochlear stimulator 160 are both be implanted within the CI user, and the communication link 240 can be a direct-wired connection or other suitable link as shown in U.S. Pat. No. 6,308,101, incorporated herein by reference.

Figure 2:
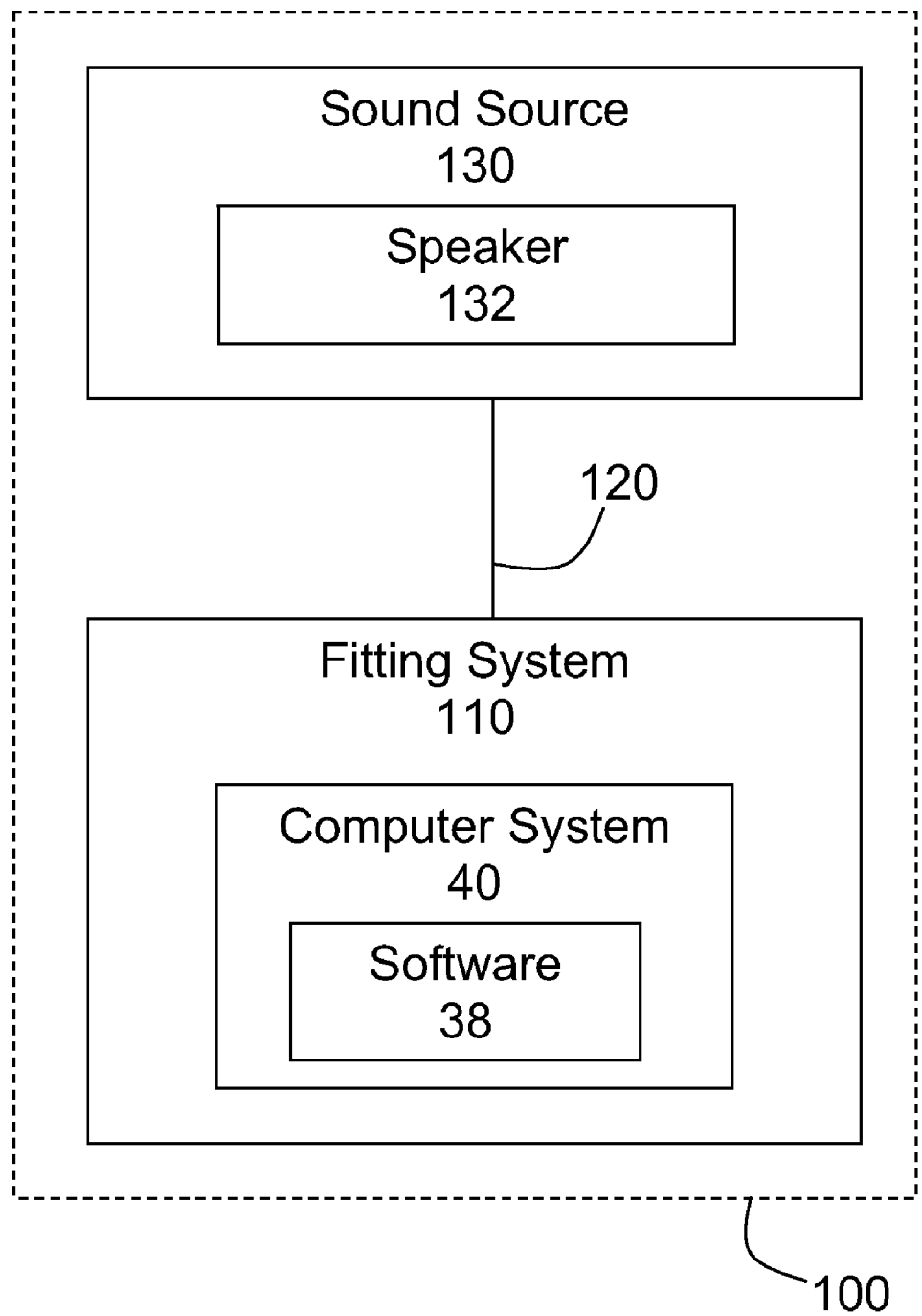
FIG. 2 is a functional block diagram showing a detailed view of a sound processing portion.

FIG. 2 depicts major subsystems of the fitting system 110. In one implementation, the fitting system 110 includes a fitting software 38 executable on a computer system 40 such as a personal computer, a portable computer, a mobile device, or other equivalent devices. The computer system 40, with or without the IU 140, generates input signals to the sound processing system 230 that stimulate acoustical signals detected by the microphone system 210. Depending on the situation, input signals generated by the computer system 40 can replace acoustic signals normally detected by the microphone system 210 or provide command signals that supplement the acoustic signals detected through the microphone system 210. The fitting software 38 executable on the computer system 40 can be configured to control reading, displaying, delivering, receiving, assessing, evaluating and/or modifying both acoustic and electric stimulation signals sent to the sound processing system 230. The fitting software 38 can generate a known acoustical signal, which can be outputted through the sound source 130. The sound source 130 can include one or more acoustical signal output devices such as a speaker 132 or equivalent devices. In some implementations, multiple speakers 132 are positioned in a 2-D array to provide directivity of the acoustical signal.

The computer system 40 executing the fitting software 38 can include a display screen for displaying selection screens, stimulation templates and other information generated by the fitting software. The some implementations, the computer system 40 includes a display device, a storage device, RAM, ROM, input/output (I/O) ports, a keyboard, and a mouse. The display screen can be implemented to display a graphical user interface (GUI) executed as a part of the software 38 including selection screens, stimulation templates and other information generated by the software 38. An audiologist, other medical personnel, or even the CI user can easily view and modify all information necessary to control a fitting process. In some implementations, the fitting portion 100 is included within the sound processing system 230 and can allow the CI user to actively perform cochlear implant front end diagnostics.

In some implementations, the fitting portion 100 is implemented as a stand alone system located at the office of the audiologist or other medical personnel. The fitting portion 100 allows the audiologist or other medical personnel to customize a sound processing strategy for the CI user during an initial fitting process after the implantation of the CI. The CI user can return to the office for subsequent adjustments as needed. The return visits may be required because the CI user may not be fully aware of his/her sound processing needs initially, and the user may need time to learn to discriminate between different sound signals and become more perceptive of the sound quality provided by the sound processing strategy. The fitting system 110 is implemented to include interfaces using hardware, software, or a combination of both hardware and software. For example, a simple set of hardware buttons, knobs, dials, slides, or similar interfaces can be implemented to select and adjust fitting parameters. The interfaces can also be implemented as a GUI displayed on a screen.

In some implementations, the fitting portion 100 is implemented as a portable system. The portable fitting system can be provided to the CI user as an accessory device for allowing the CI user to adjust the sound processing strategy as needed. The initial fitting process may be performed by the CI user aided by the audiologist or other medical personnel. After the initial fitting process, the user may perform subsequent adjustments without having to visit the audiologist or other medical personnel. The portable fitting system can be implemented to include simple user interfaces using hardware, software, or a combination of both hardware and software to facilitate the adjustment process as described above for the stand alone system implementation.

Figure 3A:
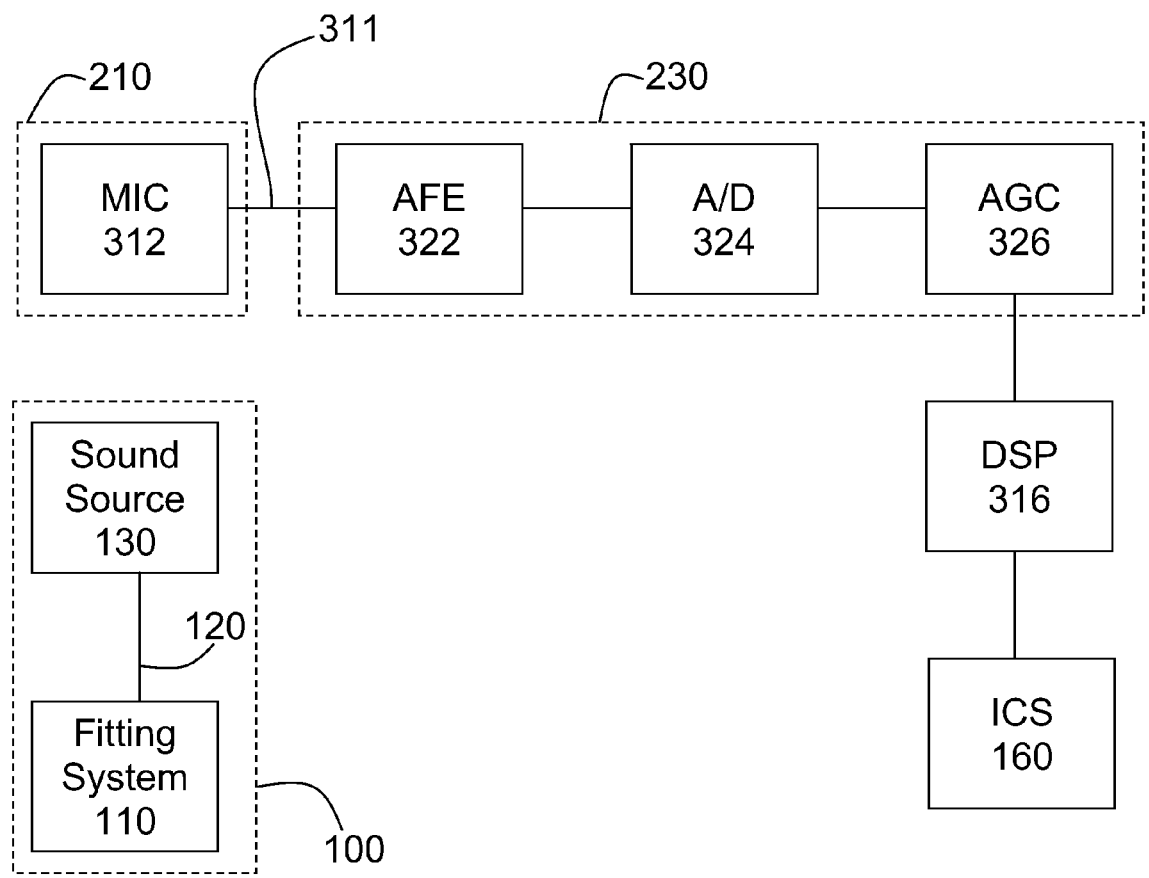
FIG. 3A is a functional block diagram describing a single signal path.
Figure 3B:
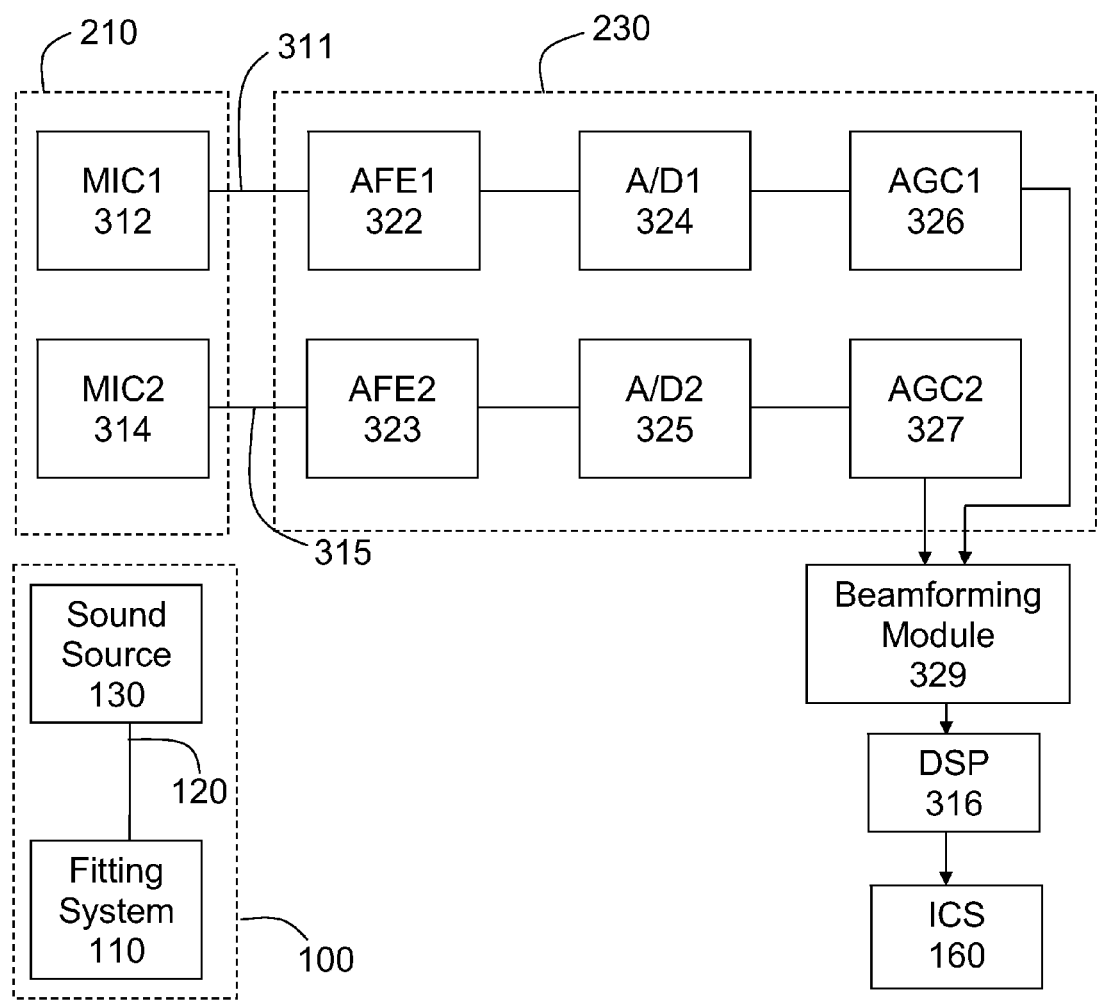
FIG. 3B is a functional block diagram describing two signal paths.

FIGS. 3A-B show a functional block diagram of the auditory front end customization system 10. FIG. 3A depicts implementations using a single microphone 312. The microphone 312 of the microphone system 210 detects a known acoustical signal outputted by the sound source 130, and the acoustical signal is converted to an electrical signal by an acoustic front end (AFE) 322. The electrical signal is presented along at least one signal path 311 of the sound processing system 230. The electrical signal is converted to a digital signal by an analog to digital converter (A/D) 324. The digitized signal is amplified by an automatic gain control (AGC) 326 and delivered to the digital signal processor (DSP) 316 to generate appropriate digital stimulations to an array of stimulating electrodes in a Micro Implantable Cochlear Stimulator (ICS) 160.

In some implementations, multiple microphones are implemented as depicted in FIG. 3B. The acoustical signals captured in each microphone 312, 314 are communicated along separate signal paths 311, 315. Each path 311 and 315 respectively includes an acoustic front end (AFE1 322 and AFE2 323), an analog to digital converter (A/D1 324 and A/D2 325), and an automatic gain control (AGC1 326 and AGC2 327). For example, in a beamforming implementation whereby two or more microphones may be implemented to provide directivity of the sound, signals from the separate signal paths 311, 315 are combined using a beamforming module 329. The combined beamforming signal is processed by the DSP 316 to generate the digital stimulations to be sent to the ICS 160.

In the implementations using multiple microphones, the microphone system 210 includes two or more microphones 312, 314 positioned in multiple locations. For example, in one implementation, the microphones 312, 314 are implemented with one internal microphone positioned internally behind the ear and one external microphone positioned near the pinnae. In an alternate implementation, a tube sound port is added to the internal microphone to align the sound pickup location with the external microphone. In yet another implementation, two internal microphones in coplanar alignment are positioned near the pinnae. In yet another implementation still, two external microphones are positioned near the pinnae. Many other combinations of internal and external microphones using different number of microphones are possible.

Figure 4:
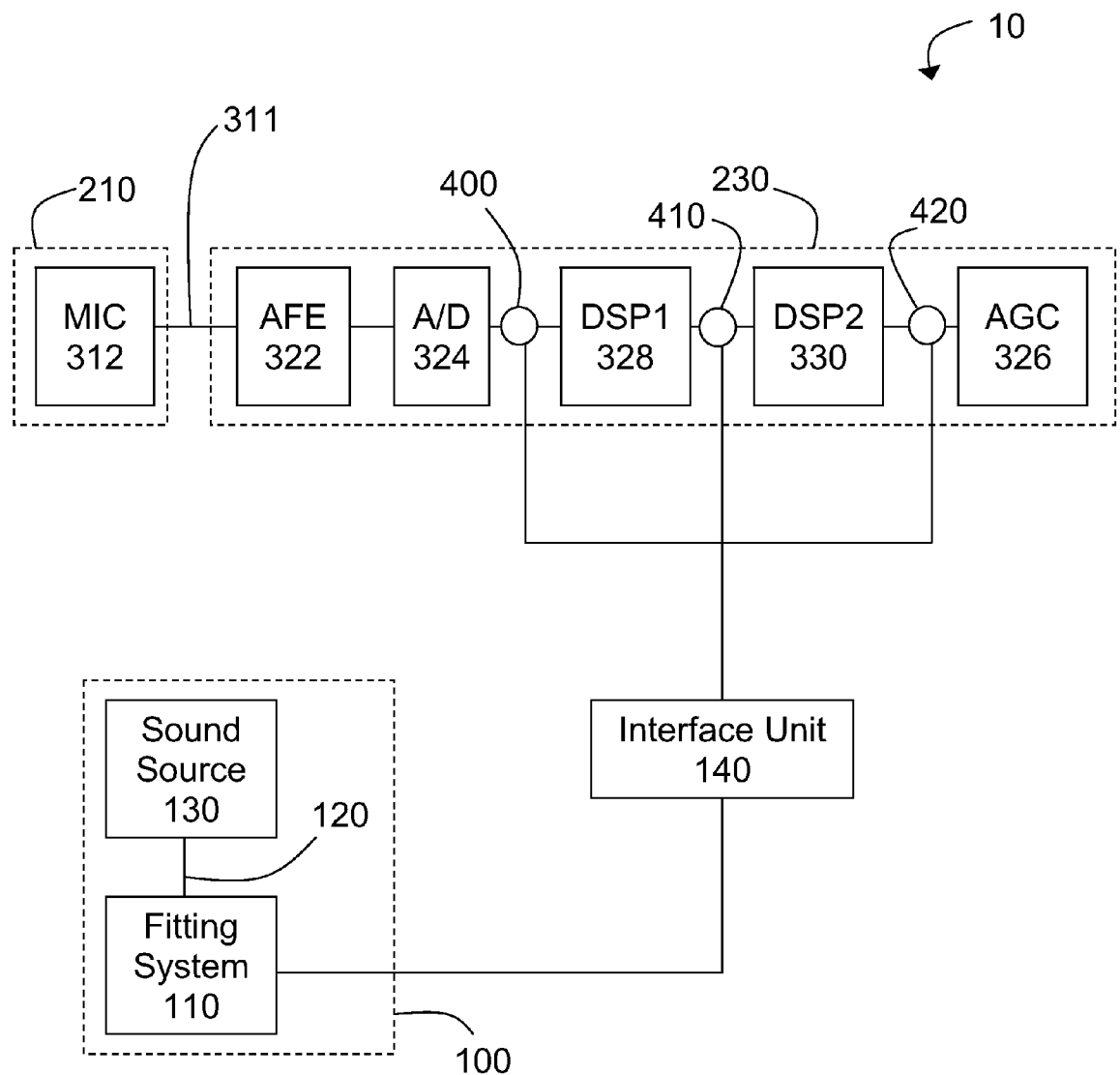
FIG. 4 is a functional block diagram of the auditory front end customization system with the possible signal sampling locations identified.

FIG. 4 depicts a block diagram of the acoustical front end customization system 10 including possible signal sampling locations 400, 410, and 420. While only a single signal pathway 311 is shown, two or more signal pathways can be implemented to process signals captured through two or more microphones. The generated known signal captured by the microphone system 210 is sampled at one or more locations 400, 410, and 420 along the signal pathway 311 of the sound processing system 230. The sampled signal(s) can be received through the IU 140 and analyzed by the fitting system 110. The sampled signal(s) is/are compared with the known acoustical signal generated by the fitting system 110 to determine an undesired spectral transformation of the sampled signal. The undesired transformation is dependent at least on the positioning of the microphones, mismatched characteristics of the microphones, and physical anatomy of the CI user's head and ear. The undesired transformation is eliminated by implementing one or more appropriate digital filters at the corresponding sampling locations 400, 410, and 420 to filter out the undesired spectral transformation of the sampled signal.

The sampling locations 400, 410, and 420 in the signal pathway 311 can be determined by the system 10 to include one or more locations after the A/D converter 324. For example, the digitized signal (after the A/D 324) can be processed using one or more digital signal processors (DSPs). FIG. 4 shows two optional DSP1 328 and DSP2 330, but the total number of DSPs implemented can vary based on the desired signal processing. DSP1 328 and DSP2 330 can be implemented, for example, as a digital filter to perform spectral modulation of the digital signal. By providing one or more sampling locations, the system 10 is capable of adapting to individual signal processing schemes unique to each CI user.

Figure 5:
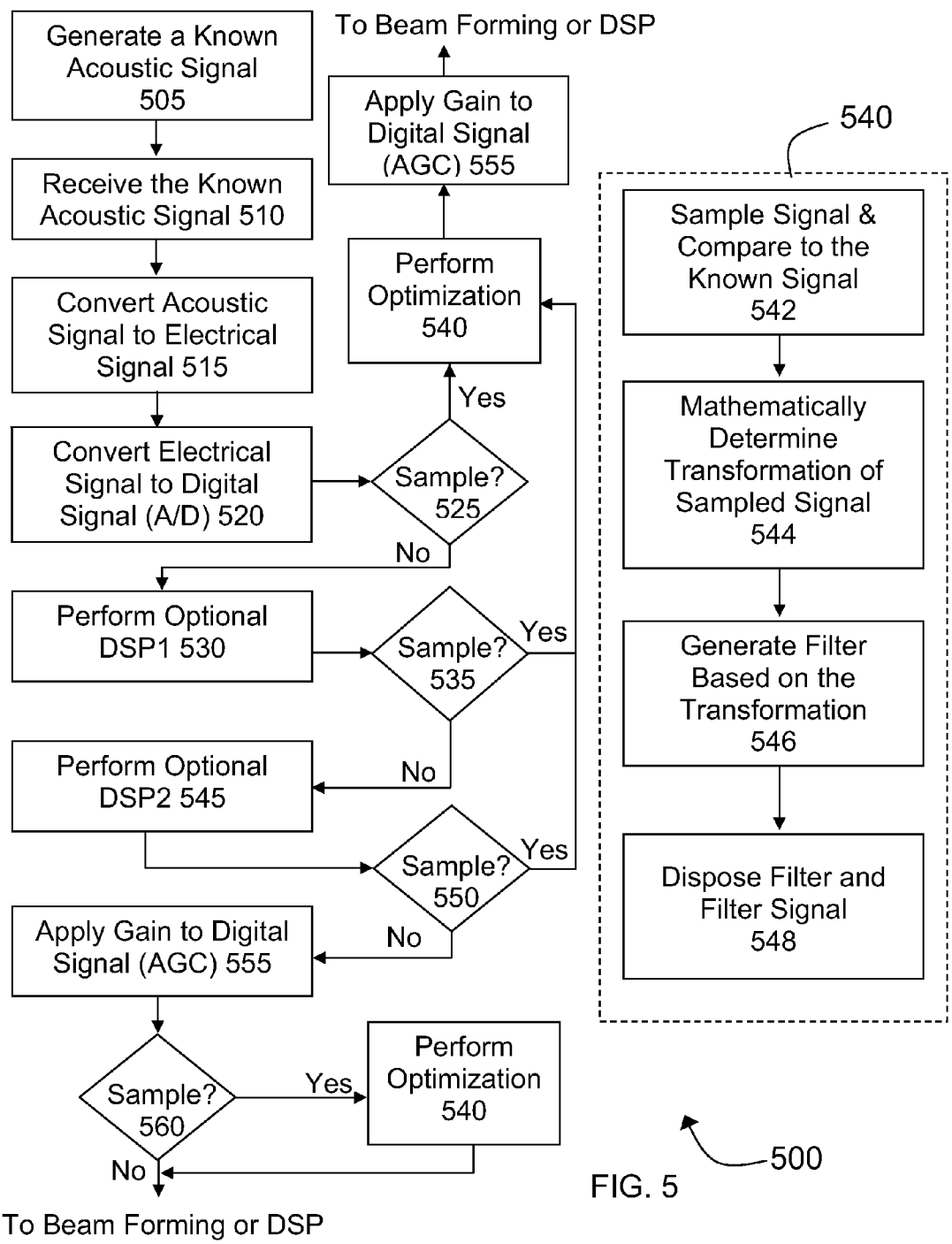
FIG. 5 is a flowchart of a process of customizing the auditory front end.

FIG. 5 depicts a flowchart 500 of a process for implementing the auditory front end customization system 10. A known acoustical signal is generated and outputted by the fitting portion 100 at 505. The known acoustical signal is received by the microphone system 210 at 510. At 515, the received acoustical signal is transformed as an electrical signal by the acoustic front end 322. Then at 520, the electrical signal is digitized via a A/D 324. A decision can be made at 525 to sample the digitized signal. If the decision is made to sample the signal, the signal is processed for optimization at 540. The optimized signal can then be forwarded to the AGC 326 at 555 before being sent to a beamforming module (now shown) or another DSP unit for generating stimulus signals.

In some implementations, optimization of the sampled signal at 540 is performed via the fitting system 110. Alternatively, in other implementations, the sound processing system 230 is implemented to perform the optimization by generating a DSP module within the sound processing system 230. In other implementations, the existing DSP module 316 is configured to perform the optimization.

Optimizing the sampled electrical signal is accomplished through at least four signal processing events. The electrical signal is sampled and a spectrum of the sampled signal is determined at 542. The determined spectrum of the sampled signal is compared to the spectrum of the known acoustical signal to generate a ratio of the two spectra at 544. The generated ratio represents the undesired transformation of the sampled signal due to the positioning of the microphones, mismatched characteristics of the microphones, and physical anatomy of the user's head and ear. The ratio generated is used as the basis for designing and generating a digital filter to eliminate the undesired transformation of the sampled signal at 546. The generated digital filter is placed at the corresponding sampling locations 400, 410, and 420 to filter the sampled signal at 548. The filtered signal is directed to the available signal processing unit on the signal path 311. The next available signal processing unit can vary depending on the signal processing scheme designed for a particular CI user.

The transfer functions and the digital filter based on the transfer functions generated through optimization at 540 can be implemented using Equations 1 through 4 below.

$$S(j\omega) = F[s(t)] = \int_{-\infty}^{+\infty} s(t)e^{-i\omega t}\, dt \quad (1)$$

$$R(j\omega) = F[r(t)] = \int_{-\infty}^{+\infty} r(t)e^{-i\omega t}\, dt \quad (2)$$

$$H(j\omega) = \frac{R(j\omega)}{S(j\omega)} \quad (3)$$

$$G(j\omega) = \frac{T(j\omega)}{H(j\omega)} \quad (4)$$

The acoustic signal or stimulus generated from the sound source 130 is s(t) and has a corresponding Fourier transform S(jω). The signal captured or recorded from the microphone system 210 is r(t) and has a corresponding Fourier transform R(jω). The acoustical transfer function from source to the microphone, H(jω), can then be characterized by Equation (3) above. If the target frequency response is specified by T(jω), then the compensation filter shape is given by Equation (4) above. This compensation filter is appropriately smoothed and then fit with an realizable digital filter, which is then stored on the sound processing system 230 at the appropriate location(s). The digital filter can be a finite-impulse-response (FIR) filter or an infinite-impulse-response (IIR) filter. Any one of several standard methods (see, e.g., *Discrete Time Signal Processing*, Oppenheim and Schafer, Prentice Hall (1989)) can be used to derive the digital filter. The entire sequence of operation just described can be performed by the fitting system 110.

In some implementations, processing events 542, 544, 546, and 548 are implemented as a single processing event, combined as two processing events or further subdivided into multiple processing events.

If the decision at 525 is not to sample the digital signal, the digital signal is forwarded to the next signal processing unit. For example, a first optional digital signal processing (DSP1) can be presented at 530. At the conclusion of the first optional digital signal processing, another opportunity to sample the digital signal can be presented at 535. A decision to sample the digital signal at 535 instructs the fitting system 110 to perform the signal optimization at 540. The signal processing events 542, 544, 546, 548 are carried out to filter out the undesired transformation and optimize the digital signal as described above. The optimized digital signal is then forwarded to the next available signal processing unit on the signal path 311. For example, the AGC 326 can be provided at 555 to protect the optimized signal against an overdriven or underdriven signal and maintain adequate demodulation signal amplitude while avoiding occasional noise spikes.

However, if the decision at 535 is not to sample the digital signal, then the digital signal can be forwarded directly to the AGC 326 and processed as described above at 555. Alternatively, another optional digital signal processing (DSP2) can be provided at 545. The gain controlled digital signal can be processed at 550 to allow for yet another sampling opportunity. If the decision at 550 is to sample the gain controlled digital signal, the sampled gain controlled digital signal can be processed by the fitting system 110 to perform the optimization at 540. The signal processing events 542, 544, and 546 are carried out on the gain controlled digital signal to filter out the undesired transformation and optimize the gain controlled digital signal as described above. The gain controlled digital signal can then be processed by the DSP module 316 and forwarded to the stimulating electrode array 170 in the ICS 160 to provide appropriate auditory nerve stimulations. If the decision at 560 is not to sample the gain controlled signal, then the signal can be directly forwarded to the DSP module 316 and the stimulating electrode array 170 in the ICS 160 as described previously.

While FIG. 4 depicts three possible sampling locations 400, 410, and 420 along the signal path 311, other sampling locations are within the scope of this disclosure. The number and location of sampling locations can partially depend on the combination of hardware and software elements implemented along the signal path 311 to perform a particular signal processing algorithm or scheme. For example, the number of optional digital signal processing units 328 and 320 can vary.

Figure 6:
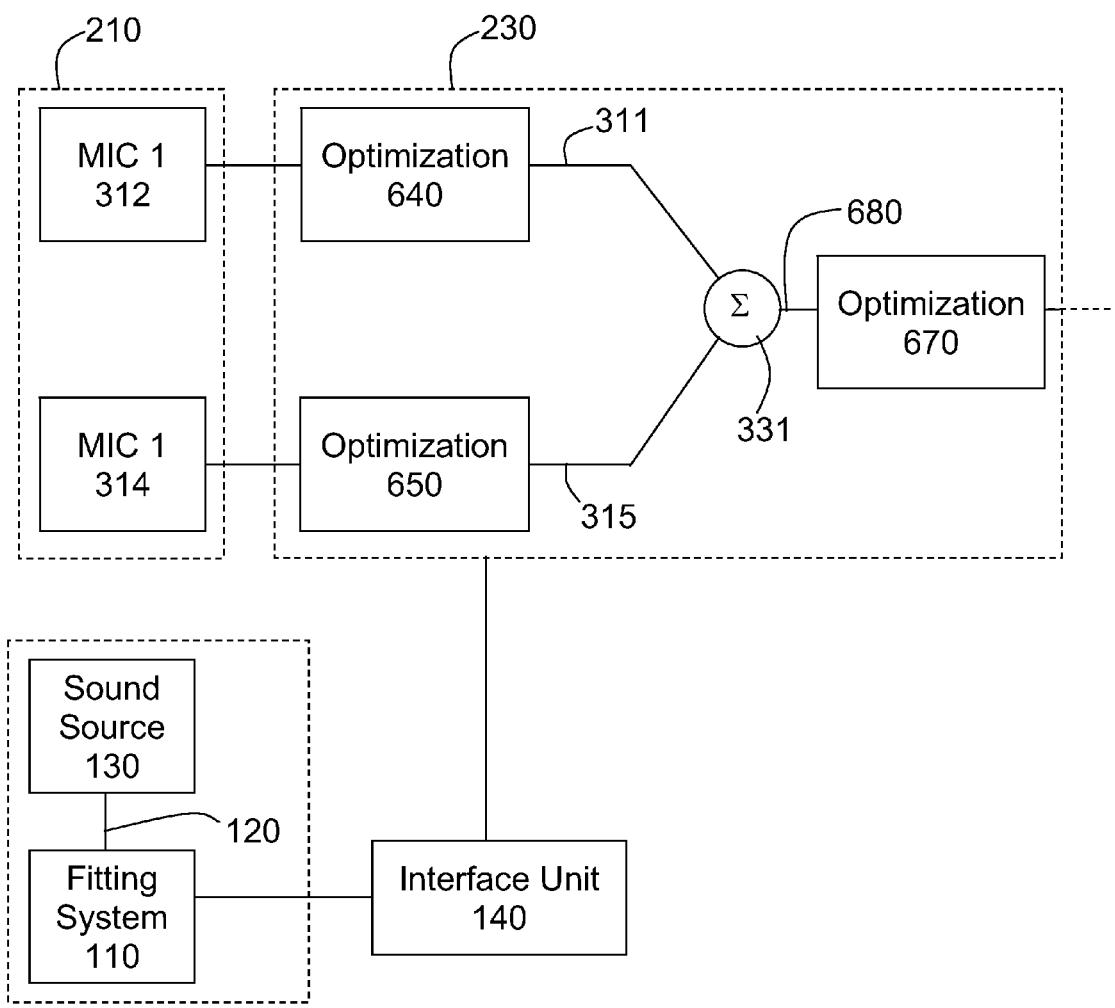
FIG. 6 presents a functional block diagram of an auditory front end customization system in a beamforming application.

Further, in implementations whereby multiple microphones are utilized, the signal processing described in FIG. 5 can be implemented in parallel along separate signal paths 311, 315 corresponding to each microphone 312, 314 as described in FIGS. 3A-B. One implementation of the auditory front end customization system 10 utilizing multiple microphones is the beamforming application. Beamforming provides directivity of the acoustical signal and allows the individual CI user to focus on a desired portion of the acoustical signal. In a noisy environment, the individual CI user can focus on the speech of a certain speaker to facilitate comprehension of such speech over confusing background noise. FIG. 6 depicts a functional block diagram of a beamforming strategy, which may be substantially as shown and described in a co-pending U.S. patent application Ser. No. 11/534,933, filed on Sep. 25, 2006, incorporated herein by reference. The microphone system 210 can include multiple microphones in various combinations of microphone types and locations. In one implementation, as represented in FIG. 6, two microphones, MIC1 312 and MIC2 314, are utilized. Separate signal paths 311 and 315 are provided for each microphone to process individual acoustical signal captured by MIC1 312 and MIC2 314. The sound processing system 230 coupled to MIC1 312 and MIC2 314 can be substantially as shown in FIGS. 3A-B above. A separate signal processing system 230 can be coupled to each microphone or alternatively a single signal processing system 230 can be coupled to both microphones.

A known acoustical signal generated by the fitting portion 100 is captured by MIC1 312 and MIC2 314, and the captured acoustical signal is processed by the sound processing system 230 in two separate signal paths 311, 315. The captured acoustical signal in signal path 311 is processed in parallel with the captured acoustical signal in signal paths 315 according to the signal processing described in FIG. 5 above. After performing the signal processing, as described in FIG. 5 above, in parallel, the processed and optimized acoustical signal in each signal path 311, 315 emerges as a processed digital signal. The processed signals are combined as a single digital beamforming signal via an adder 331. The combined beamforming signal is processed by the DSP module 316 to generate a digital stimulating signal to stimulate the array of stimulating electrodes 170 in the ICS 160 as describe above.

For the beamforming implementation, the optimization signal processing at 540 (in FIG. 5) to filter out the undesired transformation from the sampled signals is performed through optimization modules 640 and 650 placed at any of the multiple locations along the signal paths 311 and 315. In addition, the combined signal can be further optimized through an optimization module 670 placed along the combined signal path 680 to adjust for any unwanted spectral transformation in the combined beamforming signal. The unwanted spectral transformation can be quantified by computing the spectrum of the signal 680, computing the spectrum of the known acoustical signal, and computing the ratio of the two spectra. The ratio, which is now the transferfunction of the combined beamforming signal, can then be compared to a target frequency response (as in 0042 and 0043) to create a custom optimization filter.

Figure 7:
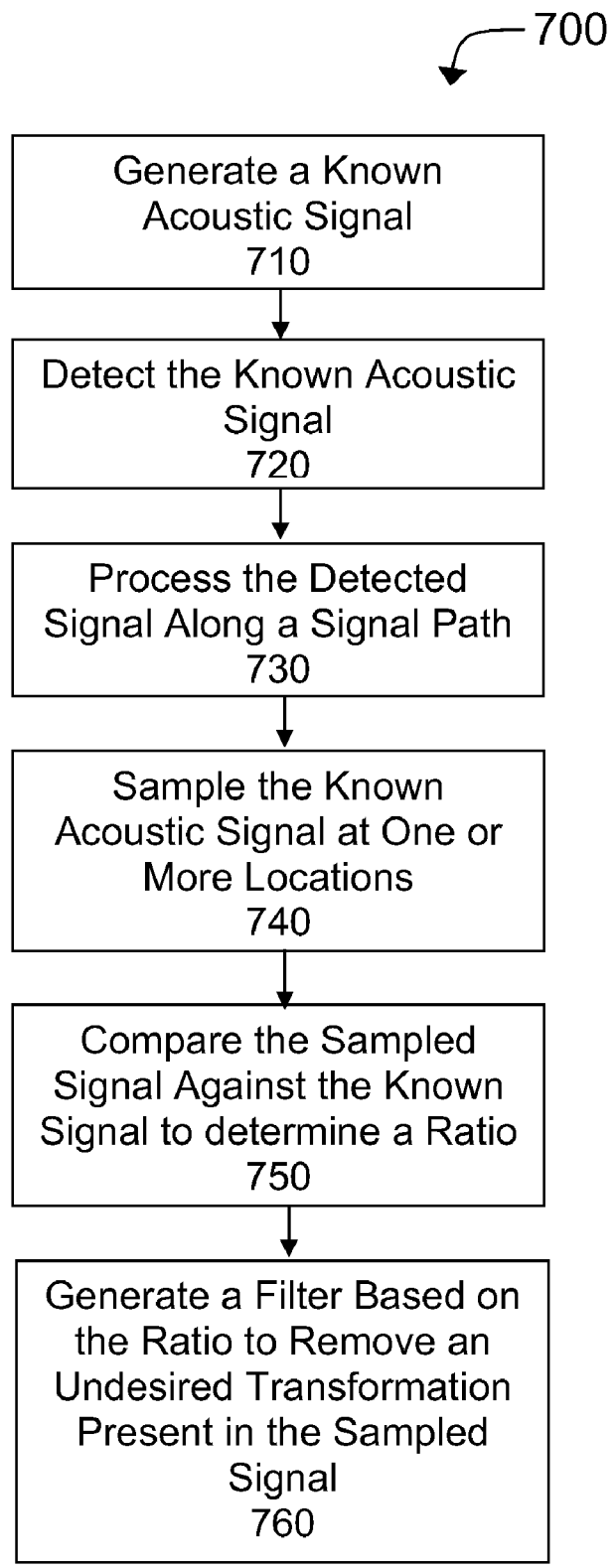
FIG. 7 is a flowchart of a generalized method of customizing the auditory front end.

FIG. 7 depicts a general process 700 for implementing cochlear implant front end customization. At 710, a known acoustic signal is generated. At 720, the generated acoustic signal is detected. The detected signal is processed along a signal path of the cochlear implant front end at 730. At 740, the processed signal is sampled at one or more locations along the signal path. The sampled signal is compared against the generated known signal to determine a ratio at 750. A filter is generated based on the ratio to filter out an undesired transformation present in the sampled signal at 760.

In some implementations, the techniques for achieving beamforming as described herein and depicted in FIGS. 1-7 may be implemented using one or more computer programs comprising computer executable code stored on a computer readable medium and executing on the computer system 40, the sound processor portion 200, or the CI fitting portion 100, or all three. The computer readable medium may include a hard disk drive, a flash memory device, a random access memory device such as DRAM and SDRAM, removable storage medium such as CD-ROM and DVD-ROM, a tape, a floppy disk, a CompactFlash memory card, a secure digital (SD) memory card, or some other storage device. In some implementations, the computer executable code may include multiple portions or modules, with each portion designed to perform a specific function described in connection with FIGS. 1-7 above. In some implementations, the techniques may be implemented using hardware such as a microprocessor, a microcontroller, an embedded microcontroller with internal memory, or an erasable programmable read only memory (EPROM) encoding computer executable instructions for performing the techniques described in connection with FIGS. 1-7. In other implementations, the techniques may be implemented using a combination of software and hardware.

Processors suitable for the execution of a computer program include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of implementations have been disclosed herein. Nevertheless, it will be understood that various modifications may be made without departing from the scope of the disclosure. Accordingly, other implementations are within the scope of the following claims.

What is claimed is:

1. A method of customizing a cochlear implant front end, the method comprising:
   receiving a known audio signal;
   sampling the received audio signal at one or more locations along one or more signal paths to generate a sampled audio signal;
   comparing the sampled audio signal against the known audio signal to detect an undesired transformation of the sampled audio signal;
   based on the comparison, generating a digital filter operative to minimize the undesired transformation of the sampled audio signal; and
   providing the generated filter in the one or more signal paths.

2. The method of claim 1, further comprising generating the known audio signal through an external sound source.

3. The method of claim 1, further comprising processing the received audio signal, wherein processing the received signal comprises:
   converting the received audio signal into an electrical signal;
   converting the electrical signal into a digital signal; and
   adjusting a gain of the digital signal.

4. The method of claim 1, wherein comparing the sampled audio signal against the known audio signal further comprises:
   determining a spectrum of the sampled audio signal;
   determining a spectrum of the known audio signal; and
   generating a ratio of the sampled audio signal spectrum over the known audio signal spectrum.

5. The method of claim 4, wherein the digital filter is generated based on the determined ratio.

6. The method of claim 1, further comprising sampling the received signal at two or more locations along one of the one or more signal paths.

7. The method of claim 1, further comprising processing the captured audio signal along two or more signal paths in parallel.

8. The method of claim 7, wherein the digital filter is generated to optimally match a first response of a first microphone with a second response of a second microphone.

9. The method of claim 8, further comprising:
   combining the matched first and second responses of the first and second microphones to generate a beamforming signal; and
   compensating for a spectral modulation of the beamforming signal.

10. A system for customizing a cochlear implant front end, the system comprising:
    a signal generator operable to generate a known audio signal;
    a microphone system operable to capture the generated audio signal;
    a signal processing system operable to process the captured audio signal along one or more signal paths;
    a signal sampler operable to sample the processed audio signal at one or more locations along one of the one or more signal paths;
    a signal comparator operable to compare the sampled audio signal against the generated known audio signal to detect an undesired transformation of the sampled audio signal; and
    a signal filter in one of the one or more signal paths operable to filter the sampled audio signal based on the comparison to minimize the undesired transformation of the sampled audio signal.

11. The system of claim 10, wherein the signal generator comprises an external sound source.

12. The system of claim 10, wherein the signal processing system further comprises:
    an auditory front end unit operable to convert the received audio signal into an electrical signal;
    an analog to digital converter operable to convert the electrical signal into a digital signal; and
    an automatic gain control operable to adjust a gain of the digital signal.

13. The system of claim 12, wherein the signal sampler is further operable to sample the processed audio signal before adjusting the gain of the digital signal.

14. The system of claim 12, wherein the signal sampler is further operable to sample the processed audio signal after adjusting the gain of the digital signal.

15. The system of claim 10, wherein the signal comparator is further operable to:
    determine a spectrum of the sampled audio signal;
    determine a spectrum of the known audio signal; and
    generate a ratio of the sampled audio signal spectrum over the known audio signal spectrum.

16. The system of claim 15, wherein the signal filter is operable to filter the sampled audio signal based on the determined ratio.

17. The system of claim 10, wherein the signal sampler is further operable to sample the processed signal at two or more locations along the one or more signal paths.

18. The system of claim 10, wherein the microphone system comprises two or more microphones, and the signal processing system is further operable to process the received audio signal along two or more signal paths in parallel.

19. The system of claim 18, wherein the signal filter is operable to optimally match a first response of a first microphone with a second response of a second microphone.

20. The system of claim 19, further comprising:
    a beamforming module operable to combined the matched first and second responses of the first and second microphones to generate a beamforming signal; and
    an optimization module configured compensate for a spectral modulation of the beamforming signal.

* * * * *